United States Patent
Pan et al.

(10) Patent No.: US 9,399,142 B2
(45) Date of Patent: Jul. 26, 2016

(54) IMPLANTABLE MEDICAL DEVICE AND SYSTEM

(71) Applicant: GIMER MEDICAL CO., LTD., Taipei (TW)

(72) Inventors: Jian-Hao Pan, Taipei (TW); Chii-Wann Lin, Taipei (TW); Chi-Heng Chang, Taipei (TW)

(73) Assignee: Gimer Medical Co., Ltd., Taipei (TW)

( * ) Notice: Subject to any disclaimer, the term of this patent is extended or adjusted under 35 U.S.C. 154(b) by 60 days.

(21) Appl. No.: 14/166,857

(22) Filed: Jan. 29, 2014

(65) Prior Publication Data

US 2015/0209590 A1     Jul. 30, 2015

(51) Int. Cl.
*A61N 1/00* (2006.01)
*A61N 1/372* (2006.01)
*A61N 1/378* (2006.01)

(52) U.S. Cl.
CPC ........... *A61N 1/37223* (2013.01); *A61N 1/3787* (2013.01); *A61N 1/37247* (2013.01)

(58) Field of Classification Search
USPC .......................................................... 607/59
See application file for complete search history.

(56) References Cited

U.S. PATENT DOCUMENTS

| | | | |
|---|---|---|---|
| 2005/0154425 A1* | 7/2005 | Boveja | A61N 1/36082 607/45 |
| 2005/0216070 A1* | 9/2005 | Boveja | A61N 1/08 607/46 |

* cited by examiner

*Primary Examiner* — Nicole F Lavert
(74) *Attorney, Agent, or Firm* — Muncy, Geissler, Olds & Lowe, P.C.

(57) ABSTRACT

The implantable medical device is for implantation into a patient's body and is wirelessly powered by an external control device. The implantable medical device is induced by an AC electromagnetic field of the external control device through an inductive coil. A rectifier converts the AC electromagnetic field into a DC current. A detector detects a voltage value of the DC current, and a processor produces a first piece of status information accordingly. A transceiver receives and relays the first piece of status information to the external control device so as to monitor the power consumption of the implantable medical device when it is wirelessly powered.

8 Claims, 2 Drawing Sheets

IMPLANTABLE MEDICAL DEVICE AND SYSTEM

BACKGROUND OF THE INVENTION (a) Technical Field of the Invention

The present invention is generally related to implantable medical devices, and more particular to an implantable medical device and system for implantation inside human bodies capable of wireless charging.

(b) Description of the Prior Art

Through the advancement of technology, medical devices have already been miniaturized so that they can be implanted inside human bodies. The clinical applications of these implantable medical devices have been gaining widespread acceptance. Active implantable medical devices such as implantable nerve stimulation devices, glucose sensors, pacemakers, etc., all require a power source where battery is a common solution. However, the lifetime of the implantable medical device depends on the capacity of the one-time battery.

Recent development has chosen to transmit power through wireless means. Wireless power suffers inferior efficiency compared to wired power. However, this is a valuable technique for implantable medical devices so that a patient is relieved from the suffering of having a surgery simply because the implantable medical device has run out of power or the battery is out of order. The operation life of the implantable medical device is also significantly enhanced.

Resonant inductive coupling is generally employed in the wireless transmission of electrical power. The transmission end and the reception end all have LC resonance mechanisms so that the transmission end is easier in producing high-power time-varying current, corresponding magnetic fluxes are induced on the inductive coils, and the reception end is easier in obtaining the transmitted energy.

When this technique is applied to the implantable medical devices, usually the reception coil has to be aligned with the transmission coil in an external control device so as to obtain the highest amount of energy. If the transmission and reception coils are perpendicular, a less amount of energy is received and the implantable medical device may not be able to function. On the other hand, the depth of the implantable medical device inside human body also affects the distance between the transmission and reception coils. Therefore, when a fixed amount of power is output from the external control device, the implantable medical device may obtain different amounts of power due to the distance and alignment between the transmission and reception coils. The received power may be too high so that the implantable medical device's temperature rises, or it exceeds the limitation of electronic components and damages the implantable medical device. The power may also be too small so that the implantable medical device cannot function correctly. The control of the transmission power is therefore an important issue.

SUMMARY OF THE INVENTION

Therefore, an implantable medical device and a related system are provided where the implantable medical device's temperature and voltage are monitored and the transmission power of the external control device is adjusted in real time so that the shortcomings of the prior art are obviated.

An implantable medical device of the present invention is for implantation into a patient's body and is wirelessly powered by an external control device. The implantable medical device contains an inductive coil, a rectifier, a detector, a processor, and a transceiver. The inductive coil is to be induced by an AC electromagnetic field of the external control device. The rectifier is electrically connected to the inductive coil, and converts the AC electromagnetic field into a DC current. The detector is electrically connected to the rectifier, detects a voltage value of the DC current, and produces a detection signal. The processor is electrically connected to the detector, receives the detection signal, and produces a first piece of status information accordingly. The transceiver is electrically connected to the processor, receives and relays the first piece of status information to the external control device.

A medical implant system of the present invention contains an implantable medical device and an external control device. The external control device contains an inductive coil, a power amplifier, a processor, and a user interface. The power amplifier is electrically connected to the inductive coil, and drives the inductive coil to resonate and to produce an AC electromagnetic field. The processor is electrically connected to the power amplifier, and transmits an operation frequency to the power amplifier. The user interface is electrically connected to the processor for user's entry of parameters into the processor.

The implantable medical device is for implantation into a patient's body. The implantable medical device contains an inductive coil, a rectifier, a detector, a processor, and a transceiver. The inductive coil is to be induced by an AC electromagnetic field of the external control device. The rectifier is electrically connected to the inductive coil, and converts the AC electromagnetic field into a DC current. The detector is electrically connected to the rectifier, detects a voltage value of the DC current, and produces a detection signal. The processor is electrically connected to the detector, receives the detection signal, and produces a first piece of status information accordingly. The transceiver is electrically connected to the processor, receives and relays the first piece of status information to the external control device.

A gist of the present invention lies in that the implantable medical device, when wirelessly powered, is not greatly affected by the depth or alignment of implantation. A desired treatment effect is as such achieved, in addition to convenient user operation.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become apparent to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
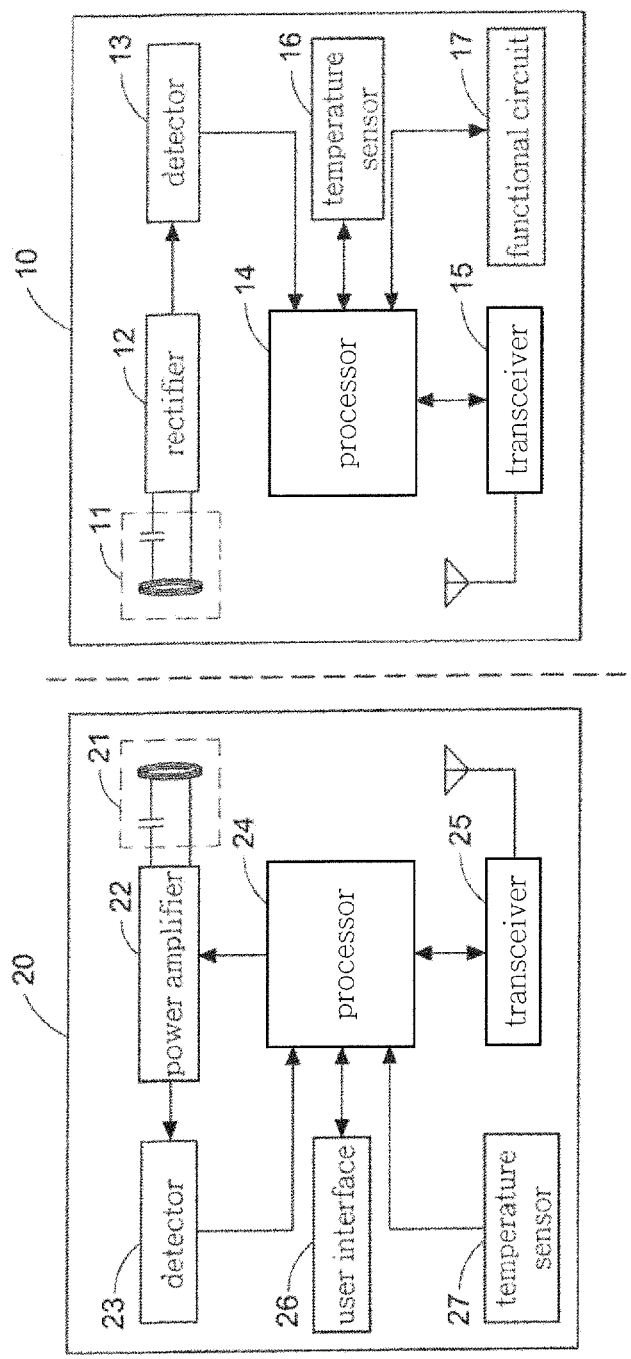
FIG. 1 is a functional block diagram of an implantable medical device according to the present invention.

FIG. 1 is a functional block diagram of an implantable medical device 10 according to the present invention. As illustrated, the implantable medical device 10 is for implantation into human body. The implantable medical device 10 can be a pacemaker or a nerve stimulation device, but is not limited as such. The implantable medical device 10 is wireless powered by an external control device 20.

The implantable medical device 10 contains an inductive coil 11, a rectifier 12, a detector 13, a processor 14, a transceiver 15, a temperature sensor 16, and a functional circuit 17. The inductive coil 11 is to be induced by an AC electromagnetic field of the external control device 20. The rectifier 12 is electrically connected to the inductive coil 11, and converts the AC electromagnetic field into a DC current. The detector 13 is electrically connected to the rectifier 12, detects a voltage value $V_{RECT}$ of the DC current, and produces a detection signal. The processor 14 is electrically connected to the detector 13, receives the detection signal, and produces a first piece of status information accordingly. The transceiver 15 is electrically connected to the processor 14, receives and relays the first piece of status information to the external control device 20. The temperature sensor 16 is electrically connected to the processor 14, and detects a temperature value of the implantable medical device 10. The functional circuit 17 is electrically connected to the processor 14. The functional circuit 17 is one for a pacemaker or a nerve stimulation device, but is not limited as such.

It should be noted that the processor 14 receives the voltage value from the detector 13, and produces a corresponding first piece of status information. Similarly, the processor 14 receives the temperature value from the temperature sensor 16, and produces a corresponding second piece of status information. On the other hand, the functional circuit 17 transmits treatment information obtained from its operation to the processor 14 which then produces a corresponding third piece of status information. Therefore, in the present embodiment, the pieces of status information could be those related to the voltage value detected by the detector 13, the temperature value sensed by the temperature sensor 16, or the treatment information from the functional circuit 17. These pieces of status information are then delivered to the external control device 20 in a wireless manner by the transceiver 15.

Figure 2:
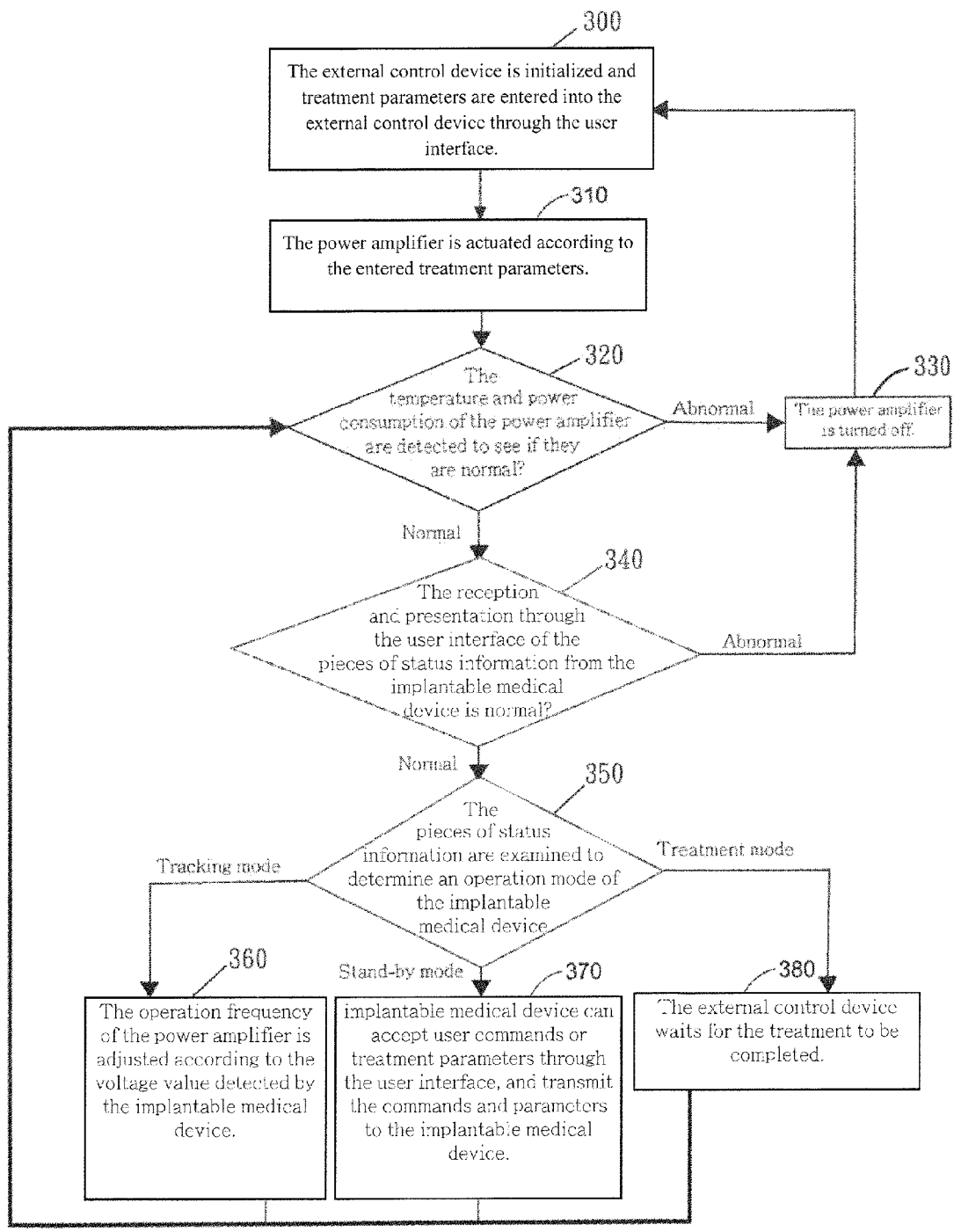
FIG. 2 is a flow diagram showing the operation of an external control device according to the present invention.

The implantable medical device 10 is implanted in the body of a patient, and the external control device 20 powers the implantable medical device 10 in a wireless manner. The external control device 20 contains an inductive coil 21, a power amplifier 22, a detector 23, a processor 24, a transceiver 25, a user interface 26, and a temperature sensor 27. FIG. 2 is a flow diagram showing the operation of the external control device 20. As illustrated in FIG. 2, the operation of the external control device 20 contains the following steps.

In step 300, the external control device 20 is initialized and treatment parameters are entered into the external control device 20 through the user interface 26.

In step 310, the power amplifier 22 is actuated according to the entered treatment parameters.

In step 320, the temperature and power consumption of the power amplifier 22 are detected to see if they are normal. If anomaly is detected, the external control device 20 enters step 330. If no anomaly is detected, the external control device 20 enters step 340.

In step 330, the power amplifier 22 is turned off and the external control device 20 returns to step 300.

In step 340, the pieces of status information are received from the implantable medical device 10, and then presented through the user interface 26. If there is anomaly in the reception, the external control device 20 returns to step 330. If there is anomaly in the reception, the external control device 20 continues to step 350.

In step 350, the pieces of status information are examined to determine an operation mode of the implantable medical device 10. If the implantable medical device 10 is in a tracking mode, a stand-by mode, or a treatment mode, the external control device 20 enters step 360, 370, or 380, respectively.

In step 360, the operation frequency of the power amplifier 22 is adjusted according to the voltage value detected by the implantable medical device 10, and the external control device 20 returns to step 320.

In step 370, the implantable medical device 10 can accept user commands or treatment parameters through the user interface, and transmit the commands and parameters to the implantable medical device 10. The external control device 20 then returns to step 320.

In step 380, the external control device 20 waits for the treatment to be completed, and then returns to step 320.

More specifically, in step 300, a user through the user interface 26 can initialize the external control device 20 and enter at least a treatment parameter into the processor 24.

More specifically, in step 310, the processor 24 receives the treatment parameters and configures an operation frequency according to the treatment parameters into the power amplifier 22. The processor 24 then actuates the power amplifier 22. Please note that the inductive coil 11 of the implantable medical device 10 and the inductive coil 21 of the external control device 20 are both series resonant LC tanks having identical resonant frequency $f_r$ expressed for example as $f_r=1/(2\pi(L_S C_S)^{1/2})$.

In other words, the external control device 20 drives the inductive coil 21 into LC resonance through the power amplifier 22 which can be a class D power amplifier, and whose operation frequency is provided by the processor 24. As such, the time-varying current on the inductive coil 21 produces magnetic flux. As the operation frequency is closer to the resonant frequency, the inductive coil 21 produces greater current, and transmits greater power.

More specifically, in step 320, the detector 23 detects the current and voltage provided to the power amplifier 22, and produces a detection signal of the power amplifier 22's power consumption to the processor 24 so as to limit the power amplifier 22's highest power. In addition, the temperature of the power amplifier 22 is detected by the temperature sensor 27 to see if it is below a pre-determined value. If the power consumption or temperature of the power amplifier 22 is beyond their pre-determined value, the power amplifier 22 is considered to be in an abnormal state, and the external control device 20 enters step 330. If the power consumption or temperature of the power amplifier 22 is under their pre-determined value, the power amplifier 22 is then considered to be in a normal state, and the external control device 20 enters step 340.

More specifically, in step 330, as the power consumption or temperature of the power amplifier 22 is beyond their pre-determined value, and the power amplifier 22 is considered to be in an abnormal state, the processor 24 turns off the power amplifier 22 and the inductive coil 21 ceases to operate. The external control device 20 returns to step 300 for initialization.

More specifically, in step 340, the inductive coil 11 of the implantable medical device 10 is induced to produce an AC current, and the rectifier 12 rectifies and regulates the AC current into a DC current so as to power the various components of the implantable medical device 10. For example, the detector 13 detects the voltage value $V_{RECT}$ of the DC current, the temperature sensor 16 detects the temperature value of the implantable medical device 10, and the functional circuit 17 transmits the treatment information obtained from its operation to the processor 14. The processor 14 produces the first, second, and third pieces of status information according to the voltage value, the temperature value, and the treatment information, and transmits these pieces of status information through the transceiver 15 wirelessly to the transceiver 25 of the external control device 20 so that the processor 24 of the external control device 20 receives the pieces of status information and then presents or updates these pieces of status information about the implantable medical device 10 through the user interface 26. Please note that, if the external control device 20 encounters anomaly during reception, the external control device 20 returns to step 330. If the external control device 20 performs reception normally, the external control device 20 enters step 350.

More specifically, in step 350, the user can examine the pieces of status information through the user interface 26. If the implantable medical device 10 is in a tracking mode, a stand-by mode, or a treatment mode, the external control device 20 enters step 360, 370, or 380, respectively.

More specifically, in step 360, if the voltage $V_{RECT}$ of the implantable medical device 10 is not between an upper bound $V_{HT}$ and a lower bound $V_{LT}$, the processor 24 modulates the operation frequency of the power amplifier 22 automatically until appropriate power is received. For example, if $V_{RECT}$ is greater than $V_{HT}$, the processor 24 produces a power reduction signal to the power amplifier 22, and the power amplifier 22 as such operates at a frequency away from the resonance frequency. If $V_{RECT}$ is lower than $V_{LT}$, the processor 24 produces a power increase signal to the power amplifier 22, and the power amplifier 22 as such operates at a frequency close to the resonance frequency. After step 360, the external control device 20 returns to step 320.

More specifically, in step 370, the voltage $V_{RECT}$ of the implantable medical device 10 is between the upper bound $V_{HT}$ and the lower bound $V_{LT}$, the power amplifier 22 is considered to operate normally, and the user can issue a command to or configure treatment parameters into the processor 24 through the user interface 26. The processor 24 can instruct the implantable medical device 10 to perform setting up or treatment. After step 370, the external control device 20 then returns to step 320.

More specifically, in step 380, the voltage $V_{RECT}$ of the implantable medical device 10 is between the upper bound $V_{HT}$ and the lower bound $V_{LT}$, the power amplifier 22 is considered to operate normally, and the implantable medical device 10 enters the treatment mode after received a treatment command. The external control device 20 waits for the treatment to be completed, and then returns to step 320.

Compared to the prior art, the detector 13 of the implantable medical device 10 can detect the voltage of the rectifier 12 in real time and transmit the voltage value to the external control device 20 in a wireless manner. The external control device 20 therefore can immediately display and adjust the output power of the power amplifier 22. The implantable medical device 10, when wirelessly powered, is not affected by the depth or alignment of implantation. A desired treatment effect is as such achieved, in addition to convenient user operation.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

We claim:

1. An implantable medical device for implantation into a human body and wirelessly powered by an external control device, the implantable medical device comprising:
    an inductive coil to be induced by an AC electromagnetic field of the external control device;
    a rectifier electrically connected to the inductive coil, and converting the AC electromagnetic field into a DC current;
    a detector electrically connected to the rectifier, detecting a voltage value of the DC current, and producing a detection signal;
    a processor electrically connected to the detector, receiving the detection signal, and producing a first piece of status information accordingly;
    a temperature sensor electrical connected to the processor, detecting a temperature value of the implantable medical device, and producing a detection signal to the processor; wherein the processor produces a corresponding second piece of status information; and
    a transceiver electrically connected to the processor, receiving and relaying pieces of status information to the external control device.

2. The implantable medical device according to claim 1, further comprising:
    a functional circuit electrically connected to the processor, wherein the processor produces a corresponding third piece of status information according to treatment information transmitted from the functional circuit.

3. A medical implant system comprising an external control device and an implantable medical device for implantation into a human body; herein
    the external control device comprises
    a first inductive coil;
    a power amplifier electrically connected to the first inductive coil, driving the first inductive coil to resonate and to produce an AC electromagnetic field;
    a first processor electrically connected to the power amplifier, and transmits an operation frequency to the power amplifier; and
    a user interface electrically connected to the first processor for user's entry of parameters into the first processor;
    the implantable medical device comprises
    a second inductive coil to be induced by the AC electromagnetic field of the external control device;
    a rectifier electrically connected to the second inductive coil, and converting the AC electromagnetic field into a DC current;
    a second detector electrically connected to the rectifier, detecting a voltage value of the DC current, and producing a detection signal;
    a second processor electrically connected to the second detector, receiving the detection signal, and producing a corresponding first piece of status information;

a second temperature sensor electrically connected to the second processor; the second temperature sensor detects a temperature value of the implantable medical device, and produces a detection signal to the second processor; and the second processor produces a corresponding second piece of status information; and a second transceiver electrically connected to the second processor, receiving and relaying pieces of status information to the external control device.

4. The medical implant system according to claim 3, wherein the external control device further comprises a first detector electrically connected to the first processor and the power amplifier; the first detector calculates a power consumption of the power amplifier and produces a detection signal to the first processor; and the first processor adjusts the operation frequency according to the detection signal.

5. The medical implant system according to claim 3, wherein the external control device further comprises a first transceiver electrically connected to the first processor; and the first and second transceivers jointly conduct the transmission of the pieces of status information through a wireless means.

6. The medical implant system according to claim 3, wherein the external control device further comprises a first temperature sensor electrically connected to the first processor; the temperature sensor detects a temperature value of the external control device and produces a detection signal to the processor; and the first processor adjusts the operation frequency according to the detection signal.

7. The medical implant system according to claim 3, wherein the implantable medical device further comprises a functional circuit electrically connected to the second processor, wherein the second processor produces a corresponding third piece of status information according to treatment information transmitted from the functional circuit.

8. The medical implant system according to claim 3, wherein the first and second inductive coils are both series resonant LC tanks having identical resonant frequency.

* * * * *